United States Patent [19]

Shaw et al.

[11] Patent Number: 4,957,593

[45] Date of Patent: Sep. 18, 1990

[54] MODIFIED COMPOSITE ELECTRODES WITH RENEWABLE SURFACE FOR ELECTROCHEMICAL APPLICATIONS AND METHOD OF MAKING SAME

[75] Inventors: Brenda R. Shaw; Kenneth E. Creasy, both of Storrs, Conn.

[73] Assignee: University of Connecticut, Storrs, Conn.

[21] Appl. No.: 319,971

[22] Filed: Mar. 7, 1989

[51] Int. Cl.$^5$ .............................................. C25B 11/12
[52] U.S. Cl. ................................... 204/291; 204/292; 204/294; 429/42
[58] Field of Search ............... 204/284, 292, 294, 291, 204/290 R, 280; 429/42

[56] References Cited

U.S. PATENT DOCUMENTS

| | | | |
|---|---|---|---|
| 3,385,780 | 5/1968 | Feng | 204/294 |
| 3,533,929 | 10/1970 | Evans et al. | 204/294 |
| 4,278,525 | 7/1981 | Gestaut | 204/294 |
| 4,337,140 | 6/1982 | Solomon | 204/294 |
| 4,339,322 | 7/1982 | Balko et al. | 204/294 |
| 4,343,767 | 8/1982 | Long et al. | 204/294 |
| 4,461,691 | 7/1984 | Frank | 204/242 |
| 4,472,257 | 9/1984 | Sklyaron et al. | 204/294 |
| 4,476,003 | 10/1984 | Frank et al. | 204/290 R |

FOREIGN PATENT DOCUMENTS 1151108 8/1983 Canada .
4541003 12/1965 Japan .................... 204/294

OTHER PUBLICATIONS

H. L. Dickstein, "Preparation of Carbon Black-Polymer Composites" University of Mass. Ph. D. Thesis, 1987.
J. Chang, et al., "Electro-Copolymerization of Acrylonitrile and Methyl Acrylate onto Graphite FIbers", Journal of Applied Polymer Science, vol. 34, 2105-2124 (1987).
R. V. Subramanian et al., "Electrodeposition of a Polymer Interphase in Carbon-Fiber Composites", Polymer Composites, Aug. 1986, vol. 7, No. 4, pp. 201-218.
R. V. Bramanian et al., "Electropolymerization on Graphite Fibers" Polymer Engineering Science, May 1978, vol. 18, No. 7, pp. 590-600.
J. Golas et al., "Carbon-Fiber Micro-Electrodes as Substrates for Mercury Films", Analytica Chimica Acta, 186 (1986) pp. 1-9.
Fathalla Belal et al., "Flow Injection Alalysis of Three N-Substituted Phenothiazine Drugs with Amperometric Detection at a Carbon Fibre-Array Electrode", Analyst, Dec. 1985, vol. 110, pp. 1493-1496
Lipka et al., "The Electrochemical Behavior of Graphite Fiber-Epoxy Composite Electrodes Containing Varying Fiber Orientations", Electrochemical Science and Technology, Feb. 1988, pp. 368-372.
Neal Sleszynski et al. "Arrays of Very Small Voltammetric Electrodes Based on Reticulated Vitreous Carbon", Analytical Chemistry, vol. 56, No. 2, Feb. 1984, pp. 130-135.
C. Amatore et al., "Charge Transfer at Partially Blocked Surfaces, A model for the Case of Microscopic Active and Inactive Sites" J. Electroanal Chemistry , #147, 1983, pp. 39-51.
Diane Welsshaar et al., "Kel-F-Graphite Composite Electrode as an Electrochemical Detector for Liquid Chromatography and Application to Phenolic Compounds", Alatlytical Chemistry, 1981, #53, pp. 1809-1813.
J. Redepenning, "Chemically Modified Electrodes: A General Overview" Trends in Analytical Chemistry, vol. 6, No. 1, 1987, pp. 18-22.
L. Santos, et al., "Electrochemistry and Chromatographic Detection of Monosaccharides, Disacharieds, and Related Compounds at an Electrocatalytic Chemically Modified Electrode", Analytica Chimica Acta, 206 (1988), pp. 85-96.

Primary Examiner—John F. Niebling
Assistant Examiner—Kathryn Gorgos

[57] ABSTRACT

Renewable modified composite electrodes for electrochemical applications are provided by homogeneous structures of a conductive filler and a modifier dispersed within a polymer matrix or binder. The modifiers may provide characteristics of electroactivity, inclusion, adsorption or electrocatalysis to the surface of the electrode in a solution. After use, the electrode may be renewed by removing a surface portion and thereby exposing a fresh portion of the homogeneous structure.

11 Claims, No Drawings

MODIFIED COMPOSITE ELECTRODES WITH RENEWABLE SURFACE FOR ELECTROCHEMICAL APPLICATIONS AND METHOD OF MAKING SAME

BACKGROUND OF THE INVENTION

The present invention relates to renewable modified composite electrodes for electrochemical applications and to methods for making same.

Modified electrodes have become of great interest because of their ability to extend the range of characteristics provided by the intrinsic interfacial properties of traditional electrodes. Such electrodes have become important tools in electroanalytical chemistry, and the uses have been expanding as new modifiers have been identified.

Heretofore, such electrodes have been prepared by application to the surface of an electrode a coating of a modifier to provide the desired alteration of the surface characteristics. In many applications, the surface layer becomes contaminated or attacked by the solution in which the electrode is immersed so that the modified electrode may not be reused. Moreover, the coating may not be uniform and, thus, produce variation in activity over the surface of the electrode. Thus, substitution of another electrode may involve some change in electrode characteristics and introduce problems of reproducibility of results.

It is an object of the present invention to provide a novel modified composite electrode which may be renewed by removing a surface portion thereof.

It is also an object to provide such an electrode which is homogeneous throughout its cross section and which may provide multiple forms of modification.

Another object is to provide a novel method for preparing such modified composite electrodes and for renewing such electrodes.

SUMMARY OF THE INVENTION

It has now been found that the foregoing and related objects and advantages may be readily attained in a renewable composite electrode for electrochemical applications which contains 1–98 percent by weight of a non-conductive polymeric matrix, and 1–98 percent by weight of a conductive filler dispersed throughout the matrix and in an amount sufficient to provide electrical conductivity in the electrode. Also disposed in the matrix is 1–98 percent by weight of a modifier providing to the electrode distinctive properties selected from the group consisting of electroactivity, inclusion, adsorption and electrocatalytic. The electrode is renewable by removal of a surface portion there of to expose a fresh portion thereof.

Most usually, the modifier is non-conductive, and the conductive filler may comprise a fibrous material or a particulate such as carbon black and metal powders.

For some applications, the modifier exhibits such properties only upon application of a potential to the electrode. In other applications, the modifier exhibits properties which will enable measurement of the potential of a solution in which immersed at zero current.

The modifiers exhibiting electroactive properties may be selected from the group consisting of organic compounds, polymers, metals and metallic compounds. The modifiers exhibiting inclusion properties are adapted to incorporate species from a solution in which immersed and are selected from the group consisting of zeolites, clays, layered compounds, polymers with ion exchange properties, and coordinating agents.

Preferably, the filler comprises 5–15 percent by weight and the modifier comprises 2–20 percent by weight of the composition.

In the method the making of renewable composite electrodes, there is produced an admixture of 1–98 parts by weight of the conductive filler 1–98 parts by weight of the modifier and 1–98 parts by weight of a matrix material selected from the group of resins and monomeric materials to produce a substantially homogeneous admixture. This admixture is subjected to conditions to convert it into a solid structure of homogeneous composition and thereby form the electrode.

In the method of use, the electrode is immersed in a solution to perform a function involving one of the properties provided by the modifier. Subsequently a portion of electrode is removed to expose fresh surface for further use.

In one procedure, the matrix material comprises a monomer formulation and the admixture is subjected to conditions to effect polymerization of the monomer formulation. In another procedure, the resin is solubilized in a solvent and admixed with the modifier and filler, and the solvent is there after removed to produce the solid electrode. There may be included the additional step of shaping the solid electrode structure by subsequent mechanical operations.

DETAILED DESCRIPTION OF THE INVENTION

The electrodes of the present invention are composites in that they are fabricated from a conductive filler in a resin matrix or binder to produce the desired conductivity, strength and surface properties. They are modified in that they utilize modifiers to impart the desired surface characteristics in the solution in which immersed.

The conductive fillers may be particulate such as carbon black, graphite and metal powders, fibrous such as carbon fibers, or metallic wire. The fillers not only provide conductivity to the composite structure but fibrous fillers also contribute to the strength, dimensional stability and other physical properties of the electrode. For some applications, the conductive filler may be a semi-conductor, i.e., one which exhibits conductivity only at certain applied potentials or temperatures. "Conductive" is meant to include the use of such semiconductors as fillers in electrodes for such special applications. Generally, particulates will have a particle size of 10–1000 millimicrons to provide good dispersability. The fibers or wires will normally have a diameter of about 0.1–100 nanometers and preferably 5–50 nonometers, and a length of at least 2 millimeters and up to the length of the electrode.

The matrix or binder is a polymer which will provide the composite with its dimensional stability and other desired properties such as resistance to excessive attack by the solutions in which immersed. Exemplary of suitable monomers are vinyl monomers such as styrenes and acrylics. The polymers may be interpolymers, and cross-linked polymers offer a high degree of stability.

Composite electrodes comprising a conductive filler and a polymer binder or matrix are known in the art. Generally, depending upon the filler and resins selected and the desired conductivity (or resistivity), the filler will comprise 1–98 percent by weight of the composition, and the matrix polymer will comprise 1-98 percent by weight. Most usually, a particulate filler will comprise 5-15 percent by weight, and the matrix polymer is 74-94 percent by weight of the composition with fibrous fillers in which higher percentages may be employed because they do not embrittle the matrix polymer.

The modifier (or modifiers) to be incorporated in the composition will depend upon the property or properties which are desired for the surface of the electrode. As has been previously indicated, one or more modifiers are included in an amount sufficient to impart the desired properties. Depending upon the modifier selected, the filler and the resin, the modifier may comprise 1-98 percent by weight of the composition, and usually it will comprise 2-20 percent by weight.

The distinctive properties imparted by the modifier offer the opportunity to utilize such renewable electrodes for various electrochemical applications, and the properties attributable to such modifiers will be recognized by those familiar with electrochemistry and electroanalytical techniques.

Electroactivity is generally considered to be the ability to oxidize or reduce the modifier when it is disposed at the surface of an electrode in contact with a solution or other medium in which it is disposed. Such modifiers may be used as electrocatalysts, as mediators, as sources of reference potentials, and as sensors of the redox potential of the surrounding solution. Exemplary of such modifiers are cobalt phthalocyanine, polymeric species such as polyvinylferrocene, metals such as silver and metal oxides such as silver oxide. Moreover, some materials may be useful as electroactive species only at certain potentials, e.g., gold amalgam, and also exhibit other desired modifier properties at other potentials.

Inclusion is generally considered to be the ability to incorporate species from the surrounding solution by ion exchange or other host-guest interactions. Such modifiers may be used as an electrocatalyst, as a support for an electrocatalyst, as a means to concentrate species from the surrounding medium, as a means of delivering species to the solution in the region surrounding the surface of the electrode, and as a potentiometric sensor for species which may be incorporated at internal or surface sites. Exemplary of such modifiers are zeolites, clays, layered double hydroxides, other layered compounds, polymeric materials with ion exchange properties, and coordinating compounds.

Adsorption is generally considered to be the ability to adsorb species from the surrounding solution by surface interactions. Such modifiers may be used as electrocatalysts, as supports for electrocatalysts, as means to concentrate species from the surrounding medium, and as a potentiometric sensor for species which are adsorbed at surface sites. Exemplary of such modifiers are layered doubled hydroxides of the formula:

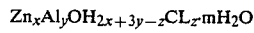

$Zn_xAl_yOH_{2x+3y-z}CL_z \cdot mH_2O$ and alumina ($Al_2O_3 \cdot mH_2O$).

Electrocatalysis is generally considered to be the ability to enhance the current for oxidation or reduction of some species in solution at a given potential or current relative to a similar electrode without the modifier. Exemplary of such modifiers are layered double hydroxides which reduce the overpotential in the oxidation of catechol and related compounds. Cobalt phthalocyanine, silver oxide, zeolites and metals supported on zeolites may serve as electrocatalysts. Gold/mercury amalgams appear suitable as catalysts for thiol oxidation and disulfide reduction.

Some modifiers may exhibit properties in more than one class of activity, or different properties in different solutions or at different pH or at different applied potentials. Moreover, modified electrodes may utilize more than one type of modifier where multiple effects are desired.

The size and thickness of the electrode formed from the composite will depend upon the application, but they should be sufficient to permit its renewal by removal of the contaminated or altered surface portion. The amount of surface to be removed will depend upon the type of contamination or alteration. Generally removal of 2-10 nanometers is required, and amounts of up to 100 nanometers may be required if the surface has been swollen by the solution. Removal of the surface may be effected by fine polishing followed by rinsing, or by slicing off a surface layer, or by any other suitable technique.

Such modified electrodes may have applications in various areas of technology where this surface modification improves the electrochemical activity. Electroanalysis is a particularly fertile application. Other applications include sensors and detectors. Moreover, such electrodes present an opportunity to improve apparatus using electrochemical activity such as fuel cells and batteries.

Several different methods for making the electrodes may be employed. The modifier, fluid resin compositive, and filler may be thoroughly admixed and disposed in molds or extruded under conditions which will convert the fluid resin composition into a solid binder or matrix for the filler. In another processing technique, the modifier may be initially adsorbed onto the filler, and the filler then mixed with, or coated with, the resin formulation after which the composition is formed into the electrodes. In still another processing variant, the filler may be initially precoated with the resin composition and the modifier then added thereto.

The particular technique utilized will generally depend upon the resin formulation and the modifier. Where polymerization is the principal mechanism being employed, and an initiator is incorporated, admixture is generally preferable.

Following formation of the electrodes, they are desirably polished to a smooth surface This may involve initial coarse sanding followed by polishing with a fine grit material. They must then be thoroughly washed.

Exemplary of the present invention are the following specific examples.

EXAMPLE ONE

Initially ground together were 4.44 parts zeolite NaA and 4.81 parts Ketjenblack (carbon black). To 89.72 parts of a mixture of 60% styrene monomer and 40% of a technical grade divinylbenzene were added 1.03 parts of 2,2 -azobis(2-methylpropionitrile) (AIBN). The powder was then admixed with the resin formulation, and the mixture was subjected to sonication for 20 minutes to ensure thorough dispersion.

The admixture was then placed into glass tubes of 3 mm. inside diameter, and the tubes were placed in vials and heated in an oven at 65° C. for 5-10 hours. Upon solidification and cooling, a gap was formed due to the differences in thermal expansion; this was filled with a fresh admixture which was then polymerized. The resultant cylindrical electrodes were removed from the tubes and polished by hand and thoroughly rinsed.

The modified composite electrodes of the present invention were then compared with modified carbon paste electrodes and with carbon paste electrodes having a coating of polystyrene containing 40% by weight zeolite A. The test involved the reduction of oxygen in an aqueous 0.2 molar potassium nitrate solution. The surface modified composite electrodes of the present invention exhibited a 71% increase in peak current over the unmodified carbon electrodes (an enhancement factor of 1.71) compared with an enhancement factor of 1.6 for the prior art coated modified electrodes.

EXAMPLE TWO

The procedure of Example One was repeated substantially with a mixture of 6.28 parts Ketjenblack, 3.77 parts alumina, 2.22 parts of AIBN and 87.73 parts of the styrene/DVB mixture.

When tested in the oxidation of a 0.003 molar solution of catechol having a pH of 3.0, the modified electrodes of the present invention greatly improved the rate of oxidation over unmodified electrodes.

EXAMPLE THREE

The procedure of Example One repeated substantially using 5.00 parts Ketjenblack, 2.77 parts layered double Hydroxide (LDH), 1.44 parts AIBN and 90.79 parts of the styrene/DVB mixture.

When tested in the oxidation of catechol as described with respect to Example Two, these modified electrodes greatly improved the rate of oxidation.

Thus, it can be seen from the foregoing detailed specification and examples that the modified composite electrodes provide highly effective electrodes with surfaces which enhance electrochemical applications. They may be fabricated relatively easily and at relatively low cost, and they may be readily renewed by removing the contaminated or affected surface.

Having thus described the invention, what is claimed is:

1. A self-supporting renewable modified composite electrode for electrochemical applications comprising a substantially homogenous structure of a composition consisting of:
   (a) 1–98 percent by weight of a non-conductive polymeric matrix;
   (b) 1–98 percent by weight of a conductive filler dispersed throughout said matrix and sufficient to provide electrical conductivity in the electrode; and
   (c) 1–98 percent by weight of a modifier dispersed throughout said matrix, said modifier providing to said electrode electroactive properties, said electrode being homogeneous throughout its cross section and thereby renewable by removal of a surface portion thereof to expose a fresh portion thereof.

2. The electrode in accordance with claim 1 wherein said modifier is non-conductive.

3. The electrode in accordance with claim 1 wherein said conductive filler comprises a fibrous material.

4. The electrode in accordance with claim 1 wherein said conductive filler comprises a particulate material.

5. The electrode in accordance with claim 1 wherein said modifier exhibits such properties only upon application of a potential to said electrode.

6. The electrode in accordance with claim 1 wherein said modifier exhibits properties which will enable measurement of the potential of a solution in which immersed at zero current.

7. The electrode in accordance with claim 1 wherein said modifier exhibiting electroactive properties is selected from the group consisting of organic compounds, polymers, metals and metallic compounds.

8. The electrode in accordance with claim 1 wherein said modifier is non-conductive and enhances electroactivity upon application of a potential to the electrode in a solution.

9. The electrode in accordance with claim 1 wherein said filler is particulate and comprises 5–15 percent by weight and said modifier comprises 2–20 percent by weight of the composition.

10. A self-supporting renewable modified composite electrode for electrochemical applications comprising a substantially homogenous structure of a composition consisting of:
    (a) 1–98 percent by weight of a non-conductive polymer matrix;
    (b) 1–98 percent by weight of a conductive filler dispersed throughout said matrix and sufficient to provide electrical conductivity in the electrode; and
    (c) 1–98 percent by weight of a modifier dispersed throughout said matrix, said modifier providing to said electrode adsorption properties, said electrode being homogeneous throughout its cross section and thereby renewable by removal of a surface portion thereof to expose a fresh portion thereof.

11. A self-supporting renewable modified composite electrode for electrochemical applications comprising a substantially homogeneous structure of a composition consisting of:
    (a) 1–98 percent by weight of a non-conductive polymeric matrix;
    (b) 1–98 percent by weight of a conductive filler dispersed throughout said matrix and sufficient to provide electrical conductivity in the electrode; and
    (c) 1–98 percent by weight of a modifier dispersed throughout said matrix, said modifier providing to said electrode electrocatalytic properties, said electrodes being homogeneous throughout its cross section and thereby renewable by removal of a surface portion thereof to expose a fresh portion thereof.

* * * * *